US008770188B2

(12) United States Patent
Stenzler et al.

(10) Patent No.: US 8,770,188 B2
(45) Date of Patent: Jul. 8, 2014

(54) METERED DOSE INHALER SPACER

(75) Inventors: Alex Stenzler, Long Beach, CA (US); Steve Han, Upland, CA (US)

(73) Assignee: CareFusion 207, Inc., San Diego, CA (US)

( * ) Notice: Subject to any disclaimer, the term of this patent is extended or adjusted under 35 U.S.C. 154(b) by 408 days.

(21) Appl. No.: 13/077,849

(22) Filed: Mar. 31, 2011

(65) Prior Publication Data

US 2012/0247460 A1    Oct. 4, 2012

(51) Int. Cl.
*A61M 15/00*    (2006.01)

(52) U.S. Cl.
USPC ............ 128/200.23; 128/200.14; 128/200.18; 128/200.22

(58) Field of Classification Search
None
See application file for complete search history.

(56) References Cited

U.S. PATENT DOCUMENTS

| 3,994,421 | A | * | 11/1976 | Hansen | 222/182 |
| 4,470,412 | A | * | 9/1984 | Nowacki et al. | 128/200.18 |
| 4,534,343 | A | * | 8/1985 | Nowacki et al. | 128/200.23 |
| 5,042,467 | A | * | 8/1991 | Foley | 128/200.23 |
| 5,676,130 | A | * | 10/1997 | Gupte et al. | 128/203.19 |
| 5,738,087 | A | * | 4/1998 | King | 128/200.23 |
| 5,816,240 | A |   | 10/1998 | Komesaroff | |
| 5,848,588 | A |   | 12/1998 | Foley et al. | |
| 6,039,042 | A |   | 3/2000 | Sladek | |
| 6,435,177 | B1 |   | 8/2002 | Schmidt et al. | |
| 6,595,206 | B2 | * | 7/2003 | Vito | 128/200.23 |
| 7,748,385 | B2 | * | 7/2010 | Lieberman et al. | 128/207.12 |
| 2003/0015195 | A1 | * | 1/2003 | Haaije de Boer et al. | 128/203.15 |
| 2008/0264412 | A1 | * | 10/2008 | Meyer et al. | 128/200.22 |
| 2011/0108025 | A1 | * | 5/2011 | Fink et al. | 128/200.16 |

OTHER PUBLICATIONS

International Search Report and Written Opinion for PCT/US2012/030470 mailed Oct. 31, 2012.

* cited by examiner

*Primary Examiner* — Tan-Uyen T Ho
*Assistant Examiner* — Eric Bryant
(74) *Attorney, Agent, or Firm* — McDermott Will & Emery LLP

(57) ABSTRACT

A metered dose inhaler (MDI) spacer has a body that defines a dose receiving chamber. A proximal end portion coupled between the body and a mouth port through which a metered dose may be inhaled by a user of the MDI spacer. A distal end portion is coupled with the body. A combined one-way and flow rate control valve coupled with the distal end portion is configured for permitting external airflow into and prohibiting internal airflow out of the dose receiving chamber. A collar coupled with the distal end portion is configured for receiving an actuator shaft of a metered dose inhaler and for forming a seal about an aerosol nozzle of the metered dose inhaler such that a metered dose of medication is admissible into the dose receiving chamber via the collar while airflow into and out of the dose receiving chamber via the collar is prohibited.

23 Claims, 7 Drawing Sheets

Section B - B

Section A - A

Section B - B

METERED DOSE INHALER SPACER

BACKGROUND

A Metered Dose Inhaler (MDI) is a device that, when actuated, emits a measured (metered) dose of an aerosolized medicine for inhalation by a patient. This dose of medicine is designed to be inhaled into the lungs of a user of the MDI. An MDI typically includes three portions, a canister for containing the medicine and propellant, an actuator shaft/aerosol nozzle for actuating the canister and metering out the dose, and a mouthpiece. Typically, the mouthpiece and actuator valve are combined into a single assembly into which the canister is inserted. When the canister is depressed, against the actuator valve, a metered dose is emitted from the canister, through the valve and out through the mouthpiece for inhalation by a user of the MDI.

An MDI spacer is a spacer that goes between the MDI and the mouth of a user of the MDI. An MDI spacer allows particles in the aerosolized dose to settle out a bit and mix with air, thus allowing for more effective delivery of a metered dose into a user's lungs when inhaled. An MDI spacer assists in preventing a user from inhaling the metered dose directly from an MDI where the dose would be traveling so fast that the particles of the aerosolized spray from the MDI hit and stick to the back of the user's throat rather than being inhaled into the user's lungs where the medicine of the metered dose is designed to be delivered.

BRIEF DESCRIPTION OF THE DRAWINGS

The accompanying drawings, which are incorporated in and form a part of this application, illustrate embodiments of the subject matter, and together with the description of embodiments, serve to explain the principles of the embodiments of the subject matter. Unless noted, the drawings referred to in this brief description of drawings should be understood as not being drawn to scale.

DESCRIPTION OF EMBODIMENTS

Reference will now be made in detail to various embodiments, examples of which are illustrated in the accompanying drawings. While the subject matter will be described in conjunction with these embodiments, it will be understood that they are not intended to limit the subject matter to these embodiments. On the contrary, the subject matter described herein is intended to cover alternatives, modifications and equivalents, which may be included within the spirit and scope. Furthermore, in the following description, numerous specific details are set forth in order to provide a thorough understanding of the subject matter. However, some embodiments may be practiced without these specific details. In other instances, well-known structures and components have not been described in detail as not to unnecessarily obscure aspects of the subject matter.

Overview of Discussion

Herein, various embodiments of a metered dose inhaler (MDI) spacer are described. The description will begin first with a discussion of the major structural components of an example MDI spacer. Attention will then be directed to subcomponents which may be combined in various embodiments or utilized all together in an embodiment. Description of the operation of an example MDI spacer and the various components and sub-components will be further explained in conjunction with discussion of a flow path for a metered, dose and inhaled, breath, and description of a flow path for exhaled breath.

Metered Dose Inhaler (MDI) Spacer

Figure 1:
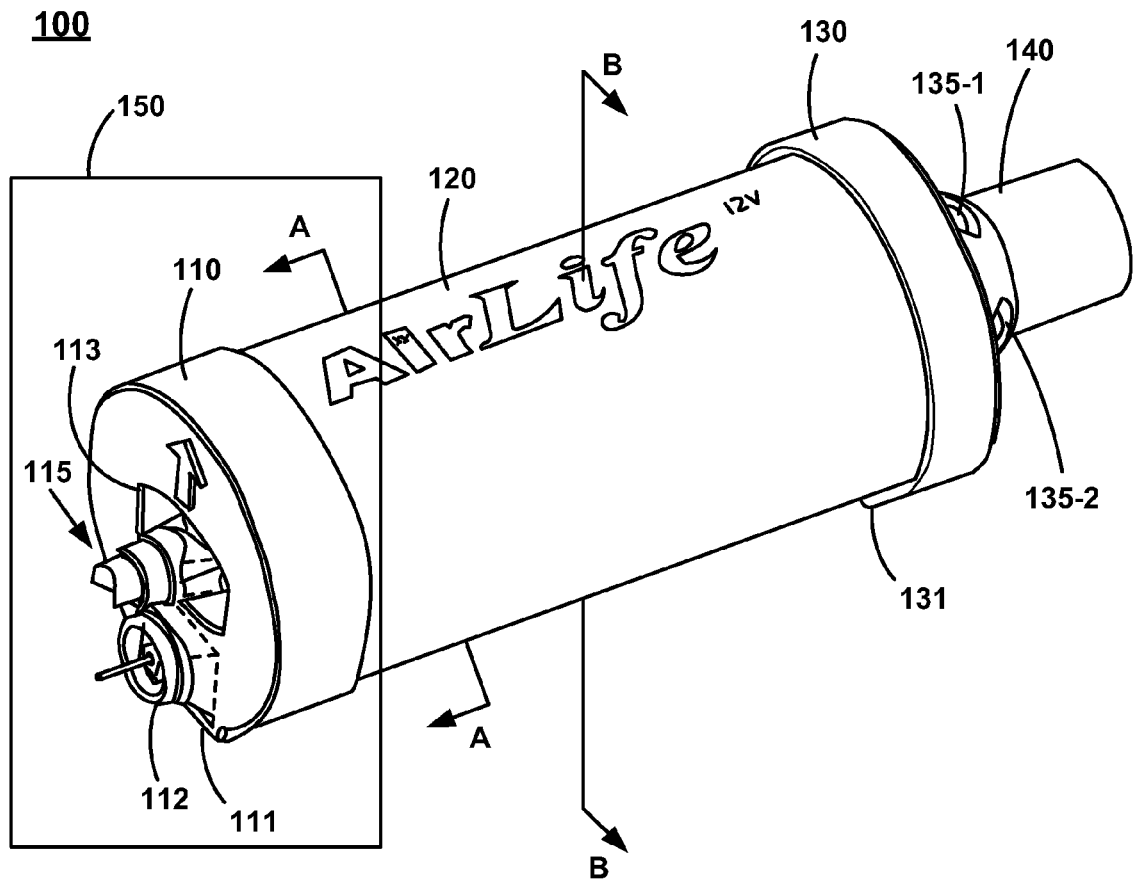
FIG. 1 shows a rear left side perspective of an example metered dose inhaler (MDI) spacer, according to an embodiment.
Figure 4:
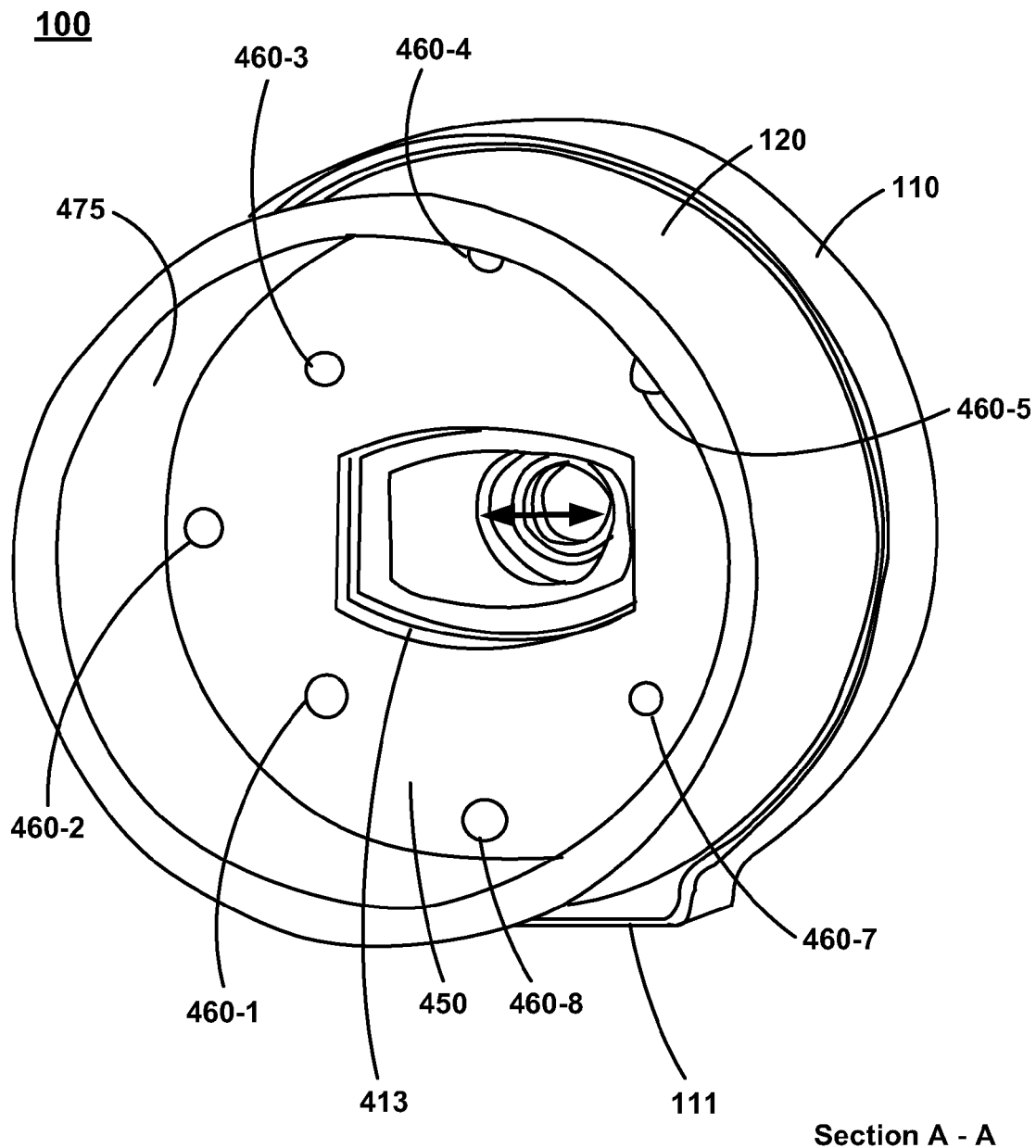
FIG. 4 is a front right side perspective and sectional view of an example MDI spacer which shows an example flat velocity profile plate, in accordance with an embodiment.
Figure 5:
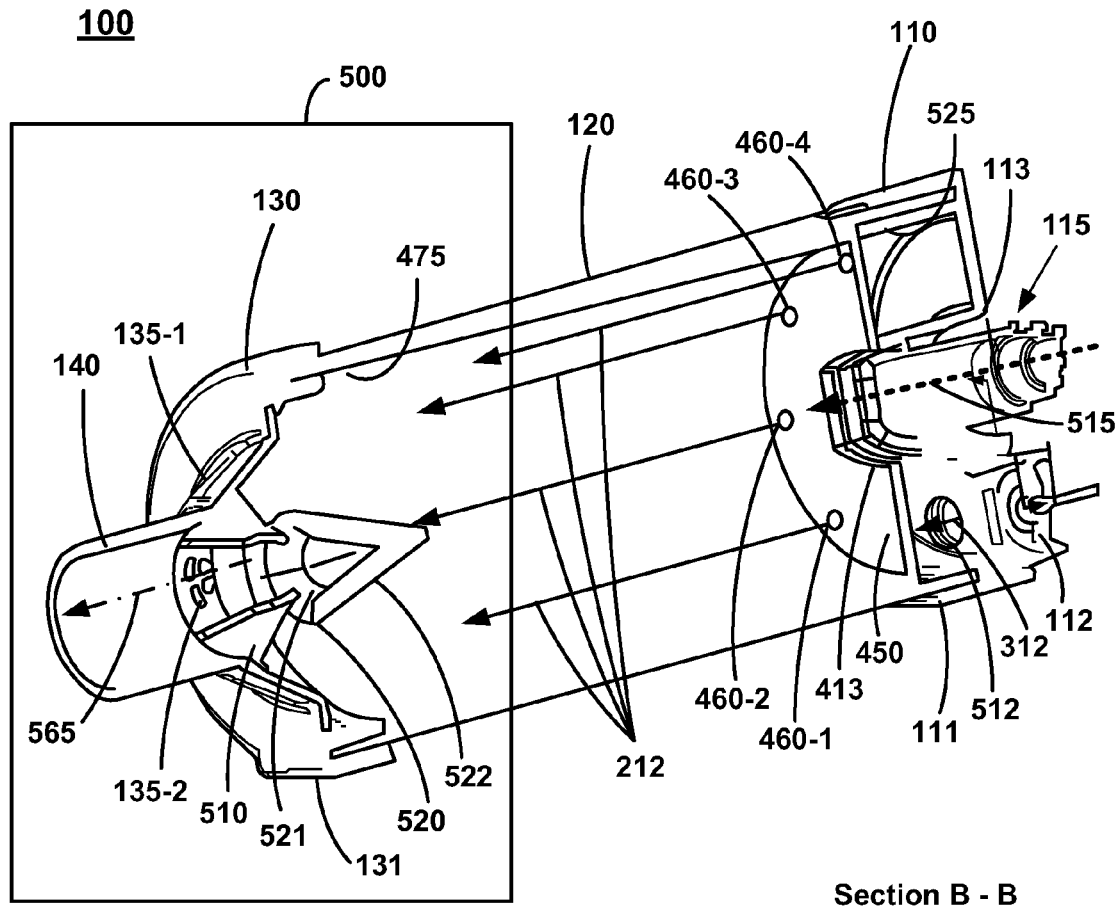
FIG. 5 is a front right side perspective and sectional view of an example MDI spacer which shows an example exhaled breath deflecting mechanism, an example flat velocity profile plate, and example flow paths of a metered dose and inhaled breath airflow, in accordance with an embodiment.
Figure 7:
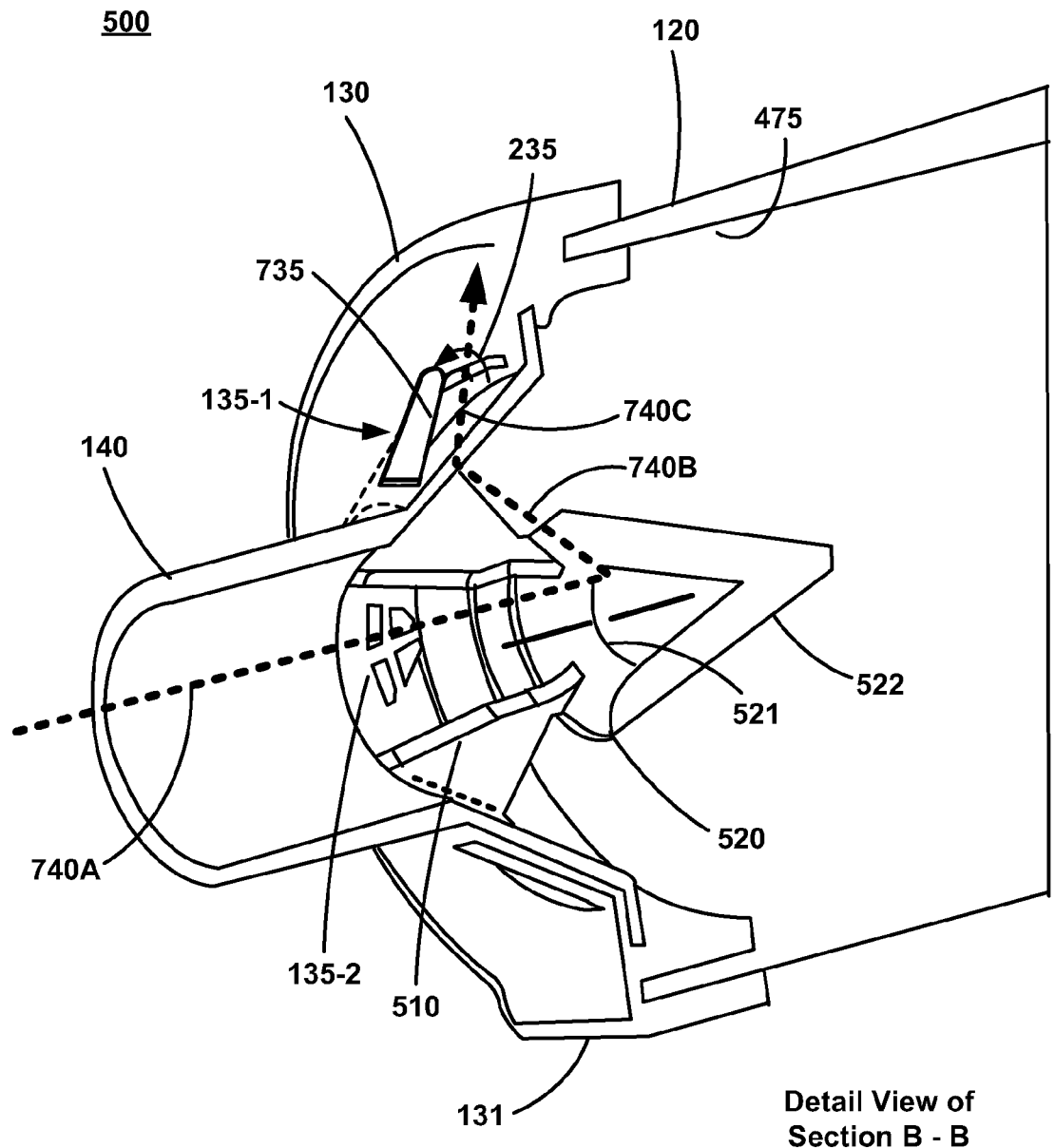
FIG. 7 is a detail view of a front right side perspective and sectional view of an example MDI spacer which shows an example exhaled breath deflecting mechanism and an example flow path of an exhaled breath airflow, in accordance with an embodiment.

FIG. 1 shows a rear left side perspective of an example MDI spacer 100, according to an embodiment. In FIG. 1, a first set of section indicators indicate the viewing direction of Section A-A, which is illustrated in FIG. 4; and a second set of section indicators indicate the viewing direction of Section B-B, which is illustrated in FIGS. 5 and 7.

As illustrated in FIG. 1, the major components of MDI spacer 100 include: a distal end portion 110, a body 120, a proximal end portion 130, and a mouth port 140. Subcomponents, which are described herein, may be coupled in various combinations with these major components to constitute various embodiments of the MDI spacers described herein. In FIG. 1, box 150 surrounds a region which is shown in enlarged detail in FIG. 3.

Body 120 defines a dose receiving chamber 475 (FIGS. 4-7) which acts as a spacer into which a metered, dose is sprayed from an MDI prior to being inhaled into the lungs of a user of MDI spacer 100. Body 120 is cylindrically shaped, and the dose receiving chamber 475 that is defined by body 120 is a substantially hollow cylinder within body 120.

Distal end portion 110 is coupled with a distal end (end farthest from the mouth of a user when MDI spacer 100 is in use) of body 120. An opening 113 is defined in distal end portion 110. Opening 113 is sized to receive the mouthpiece of a metered dose inhaler. As will be described further below, in some embodiments, a collar 115 subcomponent may be coupled with distal end portion 110 and disposed within opening 113. In some embodiments, as will be further described below, a combined one-way and flow rate control valve 112 (also referred to herein as "valve 112") subcomponent may be coupled with distal end portion 110.

Proximal end portion 130 is coupled with a proximal end (end nearest to the mouth of a user when MDI spacer 100 is in use) of body 120. Proximal end portion 130 forms a proximal end of the dose receiving chamber 475. Proximal end portion 130 opens into and couples dose receiving chamber 475 with mouth port 140. Mouth port 140 defines an opening through which a metered dose may be inhaled, from dose receiving chamber 475, by a user of MDI spacer 100. In some embodiments, mouth port 140 and distal end portion may be contiguous with one another, while in other embodiments they may be separate pieces. In some embodiments, as will be further described below, one or more expiratory valves 135 (135-1, 135-2 visible) subcomponent(s) may be coupled with or disposed within proximal end portion 130 or mouth port 140.

In some embodiments, a flat portion 111 is defined by distal end portion 110 and a similar flat, portion 131 is defined by proximal end portion 130. These flat portions 111, 131 may be positioned such that they correspond with one another to provide a base for resting MDI spacer 100, such that it does not roll around due to its otherwise substantially cylindrical shape. Flat portions 111, 131 may also be positioned to orient a MDI spacer 100 in a desired, fashion when, resting on the base formed by flat portions 111, 131.

Figure 2:
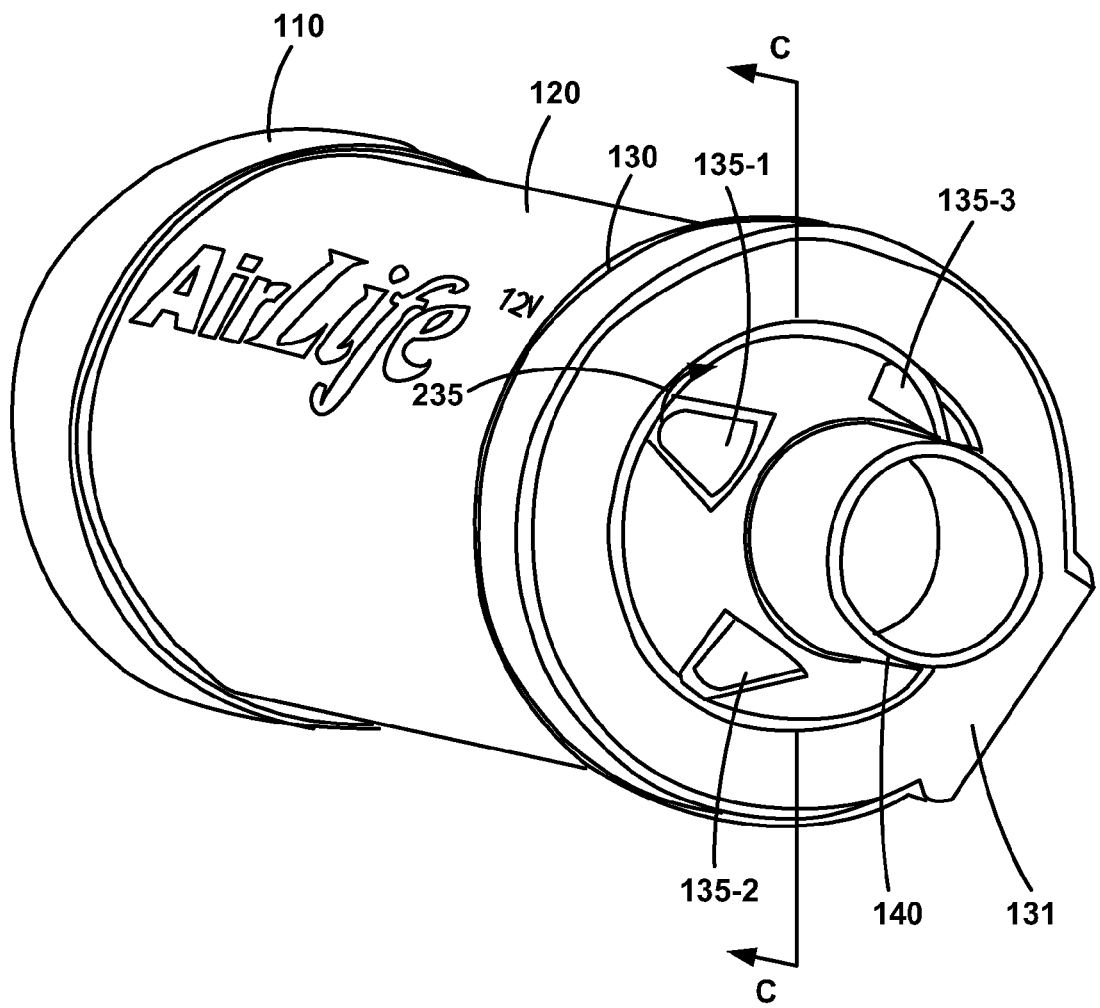
FIG. 2 is a front left side perspective view of an example MDI spacer, in accordance with an embodiment.
Figure 6:
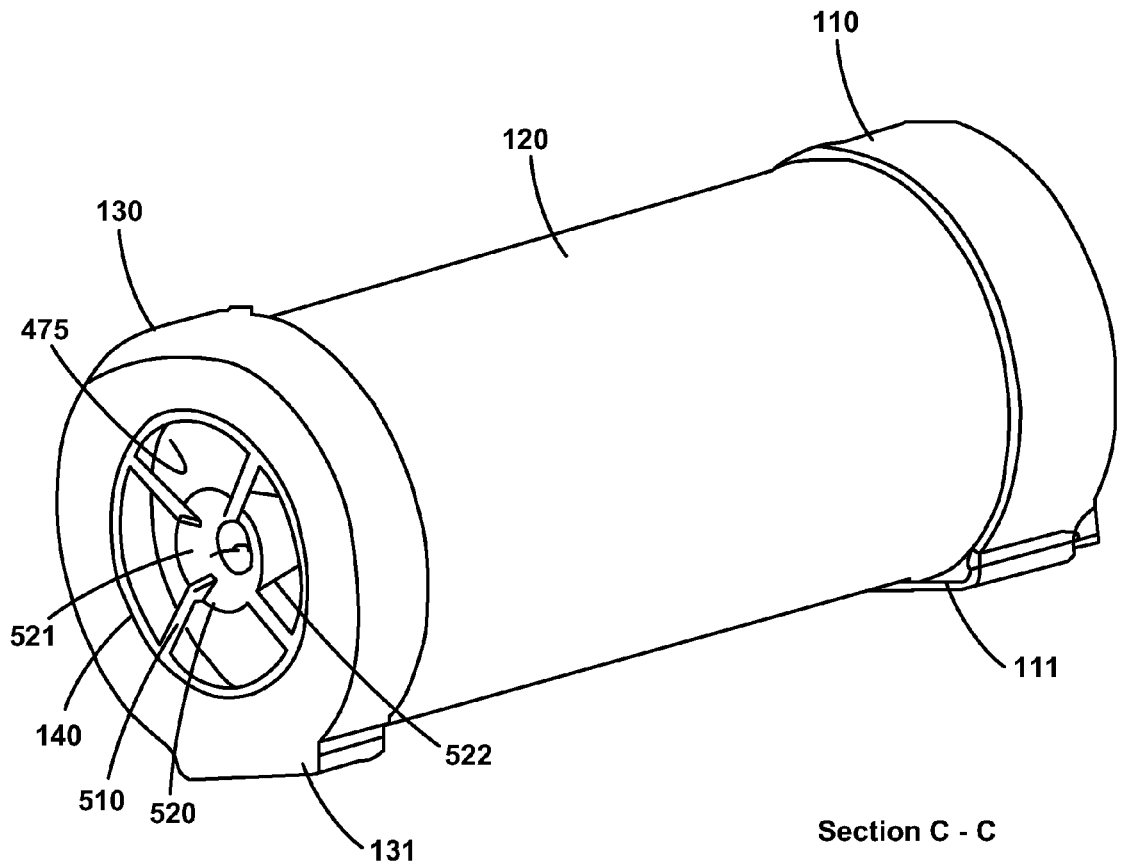
FIG. 6 is a front right side perspective and partial sectional view of an example MDI spacer which shows an example exhaled breath deflecting mechanism, in accordance with an embodiment.

FIG. 2 is a front left side perspective view of example MDI spacer 100, in accordance with an embodiment. In FIG. 2, section indicators indicate the viewing direction of Section C-C, which is illustrated in FIG. 6. FIG. 2 illustrates a third expiratory valve 135-3. Arrow 235 in FIG. 2 illustrates the direction of opening of a flexible membrane of expiratory valve 135-1 in response in response to deflected exhaled airflow.

Metered Dose Inhaler (MDI) Spacer with Sealing Dose Receiving Collar

Figure 3:
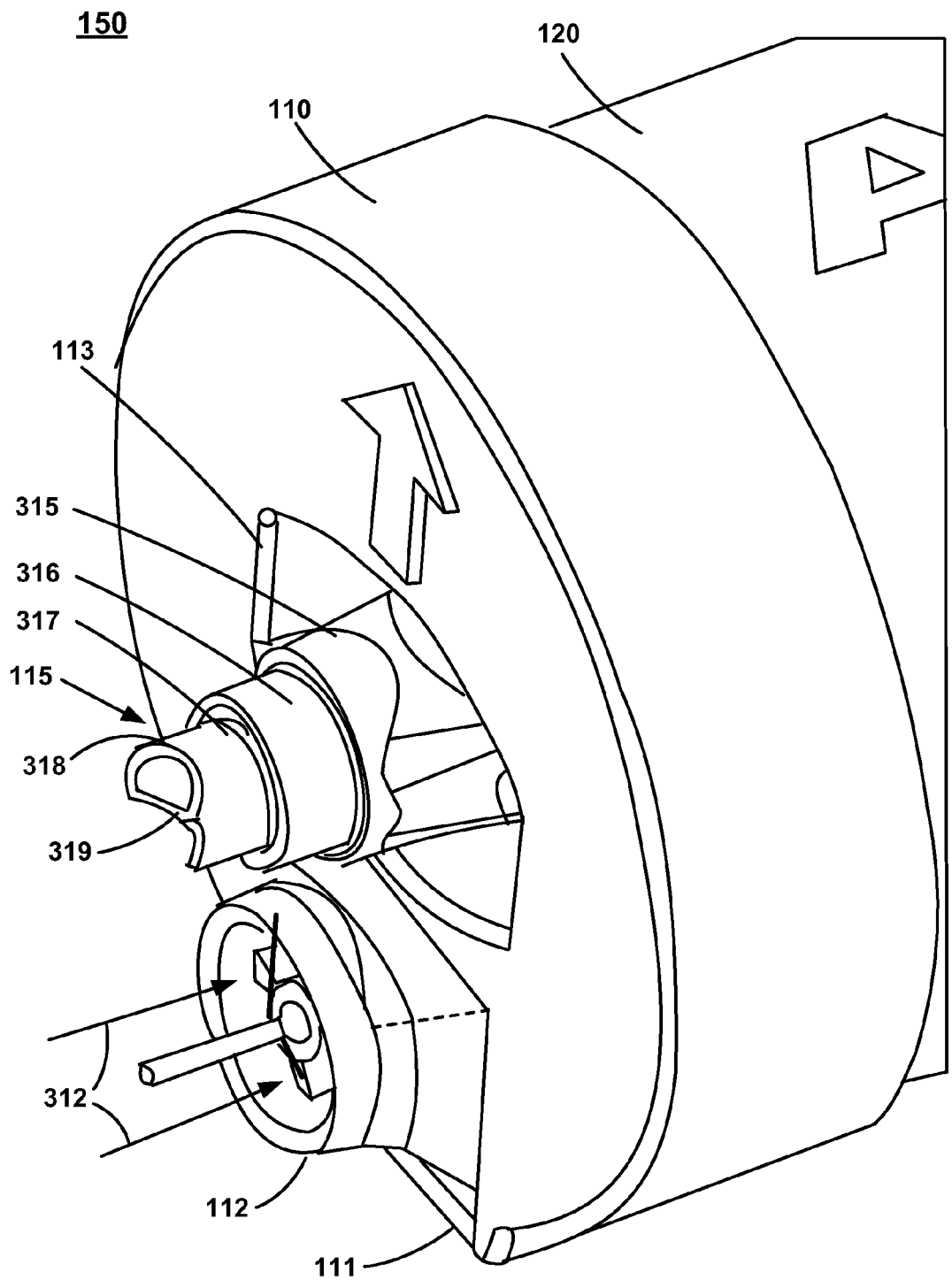
FIG. 3 is a detail view of the distal portion of the MDI spacer of FIG. 1, in accordance with an embodiment.

FIG. 3 is a detail view 150 of the distal portion of the MDI spacer of FIG. 1, in accordance with an embodiment, and shows enlarged views of valve 112 and collar 115.

Valve 112 is coupled with distal end portion 110 and configured for permitting external airflow into and prohibiting internal airflow out of dose receiving chamber 475. In some embodiments, valve 112 combines one-way airflow control function with flow rate control of the one way air flow. In other embodiments, valve 112 may only be a one-way valve or only be a flow control valve.

The one-way airflow function of valve 112 allows air to flow in toward dose receiving chamber 475 in response to user inhalation via mouth port 140, but acts as a check valve to prevent air from flowing out of dose receiving chamber 475 via valve 112 in the event that a user exhales into mouth port 140. In one embodiment, for example, the one-way airflow functionality is provided by a flexible membrane which flexes open in response to inhaled air flow caused by user inhalation via mouth port 140. Such a membrane may return to a normally closed position in the absence of inhaled air flow (thus preventing exhaled air flow through valve 112) or flex closed, against a stop in response to exhaled air flow resulting from user exhalation into mouth port 140. The one-way airflow function of valve 112 may also be implemented in a variety of other fashions that are known in the art.

The flow control function of valve 112 allows valve 112 to limit volumetric inhalation flow through valve 112 during inhalation by a user via mouth port 140. Such a flow control function may be implemented in a variety of fashions as are known. One particular example of a flow control valve, which may be utilized various embodiments of MDI spacer 100, is disclosed in U.S. Pat. No. 6,681,762, to Scheuch et al., which is incorporated herein by reference in its entirety. It is appreciated that flow rate control can be configured to limit volumetric inhalation flow rate through valve 112 to a maximum volumetric airflow rate. The maximum airflow rate at which valve 112 is set or designed to permit may be linked to a type of medication or to a dose size which is administered by a metered dose inhaler. It is appreciated that one-way airflow functionality may be inherent in the operation of some implementations of a flow rate control.

Collar 115 is coupled with distal end portion 110 and configured for receiving and removably and sealably coupling with an actuator shaft of a metered dose inhaler. Such an actuator shaft is typically formed in the shape of a hollow cylindrical post which couples with an aerosol outlet of the canister of an MDI. When the canister is depressed against the actuator shaft, a metered aerosolized dose of medicine is released, from the canister into the actuator shaft and routed perpendicularly out of the aerosol nozzle that is located at the base of the actuator shaft and inside the mouthpiece of the MDI at the base of the actuator shaft. Curved distal edges 318 and 319 of collar 115 form a seal about the actuator shaft and sealably surround the aerosol nozzle of the MDI such that a metered dose of medication flows out of the aerosol nozzle, through the interior hollow corridor of collar 115, and into dose receiving chamber 475. At the same time, this sealing action about the actuator shaft of the MDI prohibits any other airflow into and out of dose receiving chamber 475 via collar 115. Due to this sealing of collar 115 about the actuator shaft of the MDI, during metered dose administration, valve 112 is the exclusive intake point for air inflow 312 into MDI spacer 100 in response to inhalation via mouth port 140 by a user.

In one embodiment, collar 115 is disposed substantially in the center of distal end portion 110, such that a metered dose is directed via collar 115 into the center portion (of the diameter) of dose receiving chamber 475. In one embodiment, collar 115 is formed of a plurality of segments such that some segments are collapsible so that the collar 115 may self-adjust in response to being coupled with an MDI. In some embodiments, collar 115 is collapsible. FIG. 3 illustrates one example collapsible configuration of collar 115 where segment 315 is fixed and segments 316 and 317 can collapse inward toward fixed segment 315 in response to pressure applied by an MDI actuator shaft being pressed against curved distal edges 318 and 319 when the mouthpiece of an MDI is inserted into opening 113.

Metered Dose Inhaler (MDI) Spacer with Flat Velocity Profile Plate

FIG. 4 is a front right side perspective and sectional view A-A of an example MDI spacer 100 which shows an example flat velocity profile plate 450, in accordance with an embodiment. Flat velocity profile plate 450 is a subcomponent which may be included in some or all embodiments of MDI spacer 100 that are described herein. Flat velocity profile plate 450 is disposed within body 120 between valve 112 and dose receiving chamber 475 and forms a wall of a donut shaped, inflow air receiving chamber 525 (FIG. 5).

A central opening 413 is defined in flat velocity profile plate 450 and forms a portion of a sealed metered dose entrance, through collar 115, into dose receiving chamber 475. As depicted, flat velocity profile plate includes a plurality of through holes 460 (through holes 460-1, 460-2, 460-3, 460-4, 460-5, 460-7, and 460-8 are visible in FIG. 4) that are arranged around central opening 413. It is appreciated that a greater or lesser number of through holes 460, than are illustrated in FIG. 4, may be utilized. Through holes 460 permit passage of inflow air from inflow air receiving chamber 525 into dose receiving chamber 475.

Although they may appear to be of identical diameter, the diameter sizes of through holes 460 actually vary and are sized based upon respective distance from valve 112, such that each of through holes 460 provides a substantially equal air resistance (as compared with the other through holes 460) and thus normalizes air inflow velocity across the plurality of through holes 460. This normalization creates a flat velocity profile for inhaled air entering dose receiving chamber 475 via the plurality of through holes 460. In one embodiment, through holes 460 are the only avenues for entry of air inflow into dose receiving chamber 475 in response to user inhalation via mouth port 140. This flat velocity-profile surrounds central opening 413, which is the entry point for a metered dose of aerosolized medication. Due to this flat velocity profile, inhaled air inflow evenly flows through dose receiving chamber 475 at a uniform velocity, thus better mixing with aerosolized metered dose and more thoroughly sweeping the aerosolized metered dose out of dose receiving chamber 475 and into the lungs of a user than would occur in an MDI spacer which does not have a flat velocity profile for inhaled airflow.

With respect to the variance in size, in one embodiment, through holes 460 that are closer to the outlet of valve 112 into chamber 525 have a smaller diameter than through holes which are farther from the outlet of valve 112 into chamber 525. This is because the velocity of air is greater nearer the outlet of valve 112. Thus, in such an embodiment, as distance from the outlet of valve 112 increases, diameter of a through hole 460 gets progressively larger. For example, in one such embodiment, through hole 460-8 is closest to the outlet of valve 112 and therefore has the smallest diameter of any through hole 460 depicted in FIGS. 4 and 5. Through hole 460-1 is further from the outlet of valve 112 than through hole 460-8 and is thus it is slightly larger in diameter than through hole 460-8 in order to achieve the same velocity of airflow from inflow air receiving chamber 525 to dose receiving chamber 475. Through hole 460-2 is further from the outlet of valve 112 than through hole 460-1 and is thus it is slightly larger in diameter than through hole 460-1 in order to achieve the same velocity of airflow from inflow air receiving chamber 525 to dose receiving chamber 475. In some embodiments, is appreciated that other factors, such as localized volume of inflow air receiving chamber 525 proximate a particular through hole 460, may affect selection of the diameter of a particular through hole. These other factors may cause a deviation from the above example where through holes 460 get progressively larger with increased distance from the outlet of valve 112 info chamber 525.

FIG. 5 is a front right side perspective and sectional view B-B of an example MDI spacer 100 which shows an example exhaled, breath deflecting mechanism 520, an example flat velocity profile plate 450, and example flow paths of a metered dose 515 and inhaled breath airflow 212, in accordance with an embodiment. In FIG. 5, box 500 surrounds a region which is shown in enlarged detail in FIG. 7.

As is illustrated, central opening 413 is coupled with a proximal portion of collar 115 to form a sealed metered dose entrance through collar 115 and into dose receiving chamber. This sealed metered dose entrance, through collar 115, is like a tunnel that runs through inflow air receiving chamber 525, causing the volume of inflow air receiving chamber to be shaped somewhat like a donut.

Dashed arrow 515 represents an aerosolized metered dose of medication flowing into dose receiving chamber 475 via the corridor formed within hollow collar 115. In response to user inhalation via mouth port 140, inhaled breath airflow 212 flows in through valve 112 and into inflow air receiving chamber 525 via valve outlet 512. Valve 112 restricts inhaled breath airflow 212 to a maximum flow rate which cannot be increased beyond a fixed threshold by increased user inhalation. Inhaled breath airflow 212 then flows into dose receiving chamber 475 at a uniform velocity through each of a plurality of through holes 460, mixes with metered dose 515, and sweeps past the conically shaped distal surface 522 of exhaled breath deflecting mechanism 520. The conical shape of distal surface 522 presents as an aerodynamic spike to air flowing toward mouth port 140. Due to this aerodynamic shape distal surface 522 offers very little resistance to air flowing toward mouth port 140, and thus discourages adhesion of particles of medication upon distal surface 522 during user inhalation via mouth port 140. The mixture of inhaled breath airflow 212 and metered dose 515 is represented by dashed, line 565 exiting mouth port 140.

Metered Dose Inhaler (MDI) Spacer with Sealing Dose Receiving Collar

With continued reference to FIG. 5, sectional view B-B illustrates how a gap is formed between opening 113 and collar 115. This gap facilitates receipt of a mouthpiece of an MDI when collar 115 forms a seal about the actuator shaft and sealably surrounds the aerosol nozzle of the MDI. Sectional view B-B also illustrates the proximal surface 521 of exhaled breath deflecting mechanism 520. In the depicted embodiment, proximal surface 521 has a concave shape (e.g., the shape of the interior surface of a cone). In other embodiments, other concave shapes or even a flat surface or surfaces (e.g., the inferior surfaces of a pyramid), may be utilized in place of the depicted proximal surface 521 in order to deflect exhaled breath toward one or more expiratory valve 135s. One or more supports 510 couple with exhaled breath deflecting mechanism 520 and suspend it in the manner depicted such that it is centered in an inhaled airflow path toward mouth port 140 and is also centered in an exhaled airflow path that is flowing into mouth port 140 from its proximal opening.

FIG. 6 is a front right side perspective and partial sectional view C-C of an example MDI spacer 100 which shows an example exhaled breath deflecting mechanism 520, in accordance with an embodiment. This embodiment gives a better view of the overall shape and positioning of exhaled breath deflecting mechanism 520 and the size of the openings which surround it and allow airflow from dose receiving chamber 475 to freely flow into mouth port 140 in response to user inhalation via mouth port 140.

FIG. 7 is a detail view 500 of a front right side perspective and sectional view B-B of an example MDI spacer 100, which shows an example exhaled breath deflecting mechanism 520 and an example flow path 740 of an exhaled breath airflow, in accordance with an embodiment. Occasionally, a user may exhale into MDI spacer 100. This is undesirable, as exhaled breath contains a high level of moisture which may cause particles of medicine in a metered dose to stick to an interior of dose receiving chamber 475, and as exhaled breath may disturb the mixing of a metered dose of medication 515 with inhaled breath airflow 212.

To assist in preventing exhaled breath 740 from encroaching into dose receiving chamber 475, exhaled breath deflecting mechanism 520 has an angled deflecting surface 521 (concave in this embodiment), which deflects exhaled airflow 740A to create deflected, exhaled breath airflow 740B. Deflected exhaled breath airflow 740B is directed and proceeds toward the one or more expiratory valves 135 that are disposed between the proximal entry of mouth port 140 and exhaled breath deflecting mechanism 520. In FIG. 7, the response of expiratory valves 135-1 is representative of any other included expiratory valves 135 in MDI spacer 100. Membrane 735, which is fixed in place on its proximal end, is lifted (as shown by arrow 235) by the deflected exhaled airflow 740B that has been deflected by angled deflecting surface 521. Lifting of membrane 735 opens expiratory valve 135-1 and allows the exhaled airflow to escape from MDI spacer 100, as is represented by exhaled airflow 740C. Although expiratory valve 135-1 is depicted has having only a single membrane, a plurality of membranes may be employed in a similar fashion. As illustrated, expiratory valve 135-1 is operated only by deflected airflow. This is because membrane 735 lifts, and thus opens expiratory valve 135-1, only in response to deflected airflow 740B which has been deflected from angled surface 521. Membrane 735 remains closed in response to other airflow such as: inhaled breath airflow 212, metered dose 515, mixed airflow/metered dose 565, and non-deflected exhaled airflow. Additionally, because of this indirect actuation, expiratory valve(s) 135 are located outside of the airflow path of inhaled breath airflow 212, metered dose 515, and mixed airflow/metered dose 565. By locating expiratory valve(s) 135 outside of these airflow paths, expiratory valves 135 do not present targets for adhesion of medicinal particles of the metered dose during inhalation by a user of MDI spacer 100.

The foregoing descriptions of specific embodiments have been presented for purposes of illustration and description. They are not intended to be exhaustive or to limit the presented technology to the precise forms disclosed, and obviously many modifications and variations are possible in light of the above teaching. The figures and embodiments were chosen and described in order to best explain the principles of the presented, technology and its practical application, to thereby enable others skilled in the art to best utilize the presented technology and various embodiments with various modifications as are suited to the particular use contemplated. While the subject matter has been described in particular embodiments, it should be appreciated that the subject matter should not be construed as limited by such embodiments, but rather construed according to the following claims.

The invention claimed is:

1. A metered dose inhaler (MDI) spacer comprising:
a body that defines a dose receiving chamber;
a proximal end portion coupled with said body;
a mouth port coupled with said proximal end portion and through which a metered dose of medication is configured to be inhaled by a user of said MDI spacer;
a distal end portion coupled with said body;
a combined one-way and flow rate control valve coupled with said distal end portion and configured for permitting external airflow into said dose receiving chamber and prohibiting internal airflow out of said dose receiving chamber from said distal end portion;
a collar coupled with said distal end portion and configured for receiving and engaging an actuator shaft of a metered dose inhaler and forming a seal about an aerosol nozzle of said metered dose inhaler such that the metered dose of medication is conducted directly into said dose receiving chamber via said collar while airflow out of said dose receiving chamber via said distal end portion is prohibited; and
an annular disk having a center aperture and a plurality of apertures positioned about the center aperture, the annular disk being positioned within the body between said combined one-way and flow rate control valve and said dose receiving chamber such that external airflow is directed into the dose receiving chamber, prior to mixing with the metered dose of medication, via the plurality of apertures and the metered dose of medication is directed into the dose receiving chamber via the center aperture.

2. The MDI spacer of claim 1, wherein said collar is collapsible.

3. The MDI spacer of claim 1, wherein said collar is centered in said distal end portion.

4. The MDI spacer of claim 1, wherein said combined one-way and flow rate control valve is an exclusive intake point for air inflow into said MDI spacer in response to inhalation via said mouth port by said user during metered dose inhalation.

5. The MDI spacer of claim 1, wherein diameter sizes of said plurality of apertures are sized based upon respective distances from said combined one-way and flow rate control valve such that each of said plurality of apertures provides an equal air resistance and thus normalizes air inflow velocity across said plurality of apertures to create a flat velocity profile for inhaled air entering said dose receiving chamber.

6. A metered dose inhaler (MDI) spacer comprising:
a body that defines a dose receiving chamber;
a proximal end portion coupled with said body;
a mouth port coupled with said proximal end portion and through which a metered dose is configured to be inhaled by a user of said MDI spacer;
a distal end portion coupled with said body;
a channel that is configured to receive an actuator shaft of a metered dose inhaler and to conduct the metered dose directly from said actuator shaft into said dose receiving chamber;
a combined one-way and flow rate control valve coupled with said distal end portion and configured for permitting external airflow into said dose receiving chamber and prohibiting internal airflow out of said dose receiving chamber from said distal end portion; and
a flat velocity profile plate having a first opening and a plurality of through holes, the flat velocity profile plate being disposed within said body between said combined one-way and flow rate control valve and said dose receiving chamber such that external airflow is directed into the dose receiving chamber, prior to mixing with the metered dose, via the plurality of through holes and the metered dose is directed into the dose receiving chamber via the first opening.

7. The MDI spacer of claim 6, wherein said flat velocity profile plate forms a wall of a donut shaped inflow air receiving chamber.

8. The MDI spacer of claim 6, wherein the first opening comprises a central opening defined in said flat velocity profile plate and forms a portion of a sealed metered dose entrance into said dose receiving chamber.

9. The MDI spacer of claim 8, wherein said plurality of through holes are arranged around said first opening.

10. The MDI spacer of claim 6, wherein diameter sizes of said plurality of through holes are sized based upon respective distances from said combined one-way and flow rate control valve such that each of said plurality of through holes provides an equal air resistance and thus normalizes air inflow velocity across said plurality of through holes to create a flat velocity profile for inhaled air entering said dose receiving chamber.

11. A metered dose inhaler (MDI) spacer comprising:
a body that defines a dose receiving chamber;
a proximal end portion coupled with said body;
a mouth port coupled with said proximal end portion and through which a metered dose is configured to be inhaled from said dose receiving chamber by a user of said MDI spacer; and
an expiratory valve; and
an exhaled breath deflecting mechanism coupled with said mouth port in an exhaled breath airflow path and configured for deflecting and reversing exhaled breath airflow, received via said mouth port, such that said exhaled breath airflow is directed out of said MDI spacer via said expiratory valve,
wherein the exhaled breath deflecting mechanism is unresisting to an inhaled breath airflow.

12. The MDI spacer of claim 11, further comprising a plurality of expiratory valves coupled with said proximal end portion.

13. The MDI spacer of claim 11, wherein said expiratory valve is configured to open only in response to deflected exhaled breath airflow.

14. The MDI spacer of claim 11, wherein said exhaled breath deflecting mechanism comprises:
a concave exhaled breath airflow reflecting surface; and
a conical surface exposed to inhaled breath airflow.

15. A metered dose inhaler (MDI) spacer comprising:
a body that defines a dose receiving chamber;
a distal end portion coupled with said body;
a combined one-way and flow rate control valve coupled with said distal end portion and configured for permitting external airflow into and prohibiting internal airflow out of said dose receiving chamber from said distal end portion;
a collar coupled with said distal end portion and configured for receiving an actuator shaft of a metered dose inhaler and for forming a seal about an aerosol nozzle of said metered dose inhaler such that a metered dose of medication is admissible into said dose receiving chamber via said collar while airflow into and out of said dose receiving chamber via said collar is prohibited;
a flat velocity profile plate having a central opening and a plurality of through holes positioned about the central opening, the flat velocity profile plate being disposed within said body between said combined one-way and flow rate control valve and said dose receiving chamber to form a wall of an inflow air receiving chamber such that external airflow is directed into the dose receiving chamber, prior to mixing with the metered dose, via the plurality of through holes and the metered dose of medication is directed into the dose receiving chamber via the central opening;
a proximal end portion coupled with said body;
a mouth port through which the metered dose of medication is configured to be inhaled from said dose receiving chamber by a user of said MDI spacer;
an expiratory valve; and
an exhaled breath deflecting mechanism coupled with said mouth port in an exhaled breath airflow path and configured for deflecting and reversing exhaled breath airflow, received via said mouth port, out of said MDI spacer via said expiratory valve.

16. The MDI spacer of claim 15, wherein said collar is collapsible.

17. The MDI spacer of claim 15, wherein said collar is substantially centered in said distal end portion.

18. The MDI spacer of claim 15, wherein said combined one-way and flow rate control valve is an exclusive intake point for air inflow into said MDI spacer in response to inhalation via said mouth port by said user during metered dose inhalation.

19. The MDI spacer of claim 15, wherein the central opening defined in said flat velocity profile plate is coupled with said collar to form a sealed metered dose entrance through said collar and into said dose receiving chamber.

20. The MDI spacer of claim 19, wherein diameter sizes of said plurality of through holes are sized based upon respective distances from said combined one-way and flow rate control valve such that each of said through holes provides an equal air resistance and thus normalizes air inflow velocity across said plurality of through holes to create a flat velocity profile for inhaled air entering said dose receiving chamber.

21. The MDI spacer of claim 15, wherein said expiratory valve is configured to open only in response to deflected exhaled breath airflow.

22. The MDI spacer of claim 15, wherein said exhaled breath deflecting mechanism comprises:
a concave exhaled breath airflow reflecting surface; and
a conical surface exposed to inhaled breath airflow.

23. The MDI spacer of claim 11, wherein the exhaled breath deflecting mechanism is substantially centered in said proximal end portion, such that said exhaled breath deflecting mechanism is within a singular inhaled breath and exhaled breath airflow path.

* * * * *